United States Patent
Kubo

(10) Patent No.: US 8,306,754 B2
(45) Date of Patent: Nov. 6, 2012

(54) NUCLEIC ACID AMPLIFICATION DETERMINING METHOD AND NUCLEIC ACID AMPLIFICATION DETERMINING DEVICE

(75) Inventor: Kosuke Kubo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 234 days.

(21) Appl. No.: 12/810,125

(22) PCT Filed: Dec. 25, 2008

(86) PCT No.: PCT/JP2008/073536
§ 371 (c)(1),
(2), (4) Date: Jun. 22, 2010

(87) PCT Pub. No.: WO2009/081966
PCT Pub. Date: Jul. 2, 2009

(65) Prior Publication Data
US 2010/0274499 A1    Oct. 28, 2010

(30) Foreign Application Priority Data
Dec. 26, 2007    (JP) ................................ 2007-334986

(51) Int. Cl.
*G06F 19/00* (2011.01)
*G06F 15/00* (2006.01)
*C12P 19/34* (2006.01)

(52) U.S. Cl. ............................ 702/19; 435/91.2; 700/1

(58) Field of Classification Search .................. None
See application file for complete search history.

(56) References Cited

U.S. PATENT DOCUMENTS

| | | | |
|---|---|---|---|
| 6,387,621 B1 | 5/2002 | Wittwer | |
| 7,228,237 B2 | 6/2007 | Woo et al. | |
| 7,363,168 B2 | 4/2008 | Taylor et al. | |
| 7,630,837 B2 | 12/2009 | Eyre et al. | |
| 2002/0042051 A1 | 4/2002 | Wittwer | |
| 2002/0123062 A1 | 9/2002 | Wittwer | |
| 2003/0104438 A1 | 6/2003 | Eyre et al. | |
| 2003/0148302 A1 | 8/2003 | Woo et al. | |
| 2003/0148332 A1 | 8/2003 | Taylor et al. | |
| 2007/0124087 A1 | 5/2007 | Woo et al. | |
| 2007/0124088 A1 | 5/2007 | Woo et al. | |
| 2007/0192040 A1 | 8/2007 | Woo et al. | |
| 2007/0248982 A1 | 10/2007 | Woo et al. | |

FOREIGN PATENT DOCUMENTS

| | | |
|---|---|---|
| JP | 2000-333700 | 12/2000 |
| JP | 2003-180378 | 7/2003 |
| JP | 2005-504543 | 2/2005 |
| JP | 2005-058107 | 3/2005 |
| JP | 2005-516630 | 6/2005 |
| WO | 03/029924 | 4/2003 |
| WO | 03/067215 | 8/2003 |

OTHER PUBLICATIONS

Loeffler, et al., "Rapid Detection of Point Mutations by Fluorescence Resonance Energy Transfer and Probe Melting Curves in *Candida* Species", Clinical Chemistry, 2000, vol. 46, No. 5, pp. 631-635.
Chinese Office Action issued in corresponding Chinese Patent Application No. 200880023290.4 dated Mar. 23, 2012.

*Primary Examiner* — John S Brusca
(74) *Attorney, Agent, or Firm* — Morgan, Lewis & Bockius LLP

(57) ABSTRACT

The present invention provides an amplification determining method that can determine whether or not an objective nucleic acid has been amplified with respect to a sample treated so as to amplify the nucleic acid. Signal values showing molten states of the treated sample at respective temperatures are provided, and the maximum signal value (A) is searched for. Further, signal differential values at the respective temperatures are calculated by differentiation of the signal values at two successive points, and second-order differential values of the differential values are calculated by differentiation at four successive points. Among the second differential values, from those in a predetermined temperature range including a Tm value of the objective nucleic acid, the maximum second differential value ($D_{max}'$) and the minimum second differential value ($D_{min}'$) are selected. Then, the maximum difference (B) is calculated based on the formula (B)=($D_{max}'$)−($D_{min}'$). The calculation of the formula X=(B)/(A) is performed, and when X satisfies the condition [X>predetermined threshold value], the amplification is determined as normal amplification, and when X satisfies the condition [X≦predetermined threshold value], the amplification is determined as poor amplification.

18 Claims, 6 Drawing Sheets

NUCLEIC ACID AMPLIFICATION DETERMINING METHOD AND NUCLEIC ACID AMPLIFICATION DETERMINING DEVICE

TECHNICAL FIELD

The present invention relates to a method for determining nucleic acid amplification, a system for determining nucleic acid amplification, a device for determining nucleic acid amplification, a computer program that can execute the determining method on a computer, and an electronic medium storing the computer program.

BACKGROUND ART

In recent years, as a method for detecting a mutation or a polymorphism in a gene, a method for analyzing a melting curve of a double-stranded nucleic acid composed of a target nucleic acid and a probe, a melting curve analysis method, has been adopted widely. According to the melting curve analysis method, by analyzing the presence or absence of a peak at a melting temperature (Tm) of the double strand in a melting curve, the determination of a polymorphism (genotype) in a gene or the detection of the presence or absence of a mutation in a gene becomes possible.

A Tm generally is defined as below. The absorbance at 260 nm increases as a solution containing a double-stranded nucleic acid is heated. This increase is caused by the fact that the hydrogen bond between both the strands in a double-stranded nucleic acid is released by heating, and the double-stranded nucleic acid is dissociated into single-stranded nucleic acids (melting of a double-stranded nucleic acid). When every double-stranded nucleic acid is dissociated into single-stranded nucleic acids, the solution exhibits an absorbance about 1.5 times as large as the absorbance at the time when the heating was initiated (the absorbance of the solution containing only the double-stranded nucleic acid), whereby it can be determined that the melting is completed. Based on this phenomenon, a melting temperature Tm (° C.) generally is defined as a temperature at the time when the amount of increase in absorbance reaches 50% of the total amount of increase in absorbance.

By utilizing this nature of a double-stranded nucleic acid, a polymorphism or a mutation in a target site can be detected in the following manner, for example. That is, it can be achieved by the method in which, using a mutant-type detection probe that is complementary to a target nucleic acid sequence containing a mutant-type target site, a double stranded nucleic acid composed of a single-stranded nucleic acid to be analyzed and the probe is formed, the formed double-stranded nucleic acid is heat-treated, the dissociation of the double strand with temperature increase is detected by measuring signal values such as absorbance and the like, and the presence or absence of a mutation in the target site is determined by the behavior of the signal at a Tm value based on the detection result (ref. Non Patent Citation 1 and Patent Citation 1). Thus, the Tm value becomes higher as the homology of a double-stranded nucleic acid becomes higher and becomes lower as the homology of a double-stranded nucleic acid becomes lower. Thus, as evaluation criteria, Tm values of a double-stranded DNA composed of a target nucleic acid sequence with a mutant-type target site and a mutant-type detection probe that is 100% complementary to the target nucleic acid sequence and a Tm value of a double-stranded DNA composed of a nucleic acid sequence with a wild-type target site and the mutant-type detection probe are determined previously. Since the Tm value becomes higher as the homology of a double-stranded nucleic acid becomes higher as described above, the former, i.e., the Tm value in the case where the target site is of mutant type (hereinafter, also referred to as "$Tm_m$ value") is relatively high and the latter, i.e., the Tm value in the case where the target site is of wild type (hereinafter, also referred to as "$Tm_w$ value") is relatively low. Subsequently, a melting curve of the double-stranded nucleic acid composed of the single-stranded nucleic acid to be analyzed and the mutant-type detection probe is prepared, and whether a peak is present at the previously determined $Tm_m$ value or at the previously determined $Tm_w$ value is checked. When the peak is present at around the $Tm_m$ value, the nucleic acid sequence is a 100% match to the mutant-type detection probe, whereby the single-stranded nucleic acid to be analyzed can be determined as having a mutant-type polymorphism. On the other hand, when the peak is present at around the $Tm_w$ value, the nucleic acid sequence is a mismatch to the mutant-type detection probe in a single base, whereby the single-stranded nucleic acid to be analyzed can be determined as having a wild-type polymorphism. Further, whether the polymorphism is homozygous or heterozygous also can be determined. That is, in an analysis of a pair of alleles, when peaks are present at both around the $Tm_m$ value and around the $Tm_w$ value, the polymorphism can be determined as being heterozygous. On the other hand, when a peak is present at only around the $Tm_m$ value, the polymorphism can be determined as being a mutant-type homozygous, and when a peak is present at only around the $Tm_w$ value, the polymorphism can be determined as being a wild-type homozygous.

To conduct such melting curve analysis, usually, an amplification treatment of the target nucleic acid sequence is conducted with respect to a sample containing RNA or DNA, and the obtained amplification product is subjected to double strand formation with the probe and the disassociation by heating as described above. However, when the target nucleic acid sequence cannot be amplified sufficiently in the amplification treatment, there arises a problem that the polymorphism is determined incorrectly. Thus, in a conventional method, with respect to a sample after being subjected to the amplification treatment, a graph of a melting curve showing the relationship between each temperature and a signal value showing the molten state of the sample or a differential value of the signal value (hereinafter referred to as "signal differential value") is prepared, and whether or not a peak is present at around $Tm_m$ value or $Tm_w$ value is determined by visual observation. However, since specialized knowledge is required in order to make such determination in the gene analysis, it is difficult to determine easily whether what is observed is a peak or not, for example. Further, in the case of visual observation, the fact that criteria of determination vary between individuals has been perceived as a problem. Therefore, in the conventional method, the analysis has to be conducted also with respect to a sample in which nucleic acid amplification has not been conducted normally, and the labor required therefor is perceived as a problem. For such reasons, it is difficult to expand the application of a gene analysis and a gene diagnosis utilizing the melting curve analysis to the field of general analysis and diagnosis. Further, it is also difficult to analyze multiple specimens all at once from the viewpoint of its specialty or the like.

Non Patent Citation 1: Clinical Chemistry, 2000 46 (5): p. 631-635

Patent Citation 1: JP 2005-58107 A

DISCLOSURE OF INVENTION

Hence, the present invention is intended to provide an amplification determining method that can determine whether or not an objective nucleic acid has been amplified with respect to a sample treated so as to amplify the nucleic acid. Further, the present invention is intended to provide an amplification determining system, an amplification determining device, a program, and an electronic medium for executing the foregoing amplification determining method.

In order to achieve the aforementioned object, the amplification determining method of the present invention is an amplification determining method for determining whether or not an objective nucleic acid has been amplified with respect to a sample treated so as to amplify the nucleic acid. The method includes the steps of:

providing signal values showing molten states of the treated sample at respective temperatures;

searching for a maximum value (A) in the signal values at the respective temperatures;

calculating differential values of the signal values at the respective temperatures by differentiation of successive signal values;

calculating second-order differential values of the differential values calculated in the above step by differentiation of successive differential values;

calculating a maximum difference (B) among the second-order differential values by selecting a maximum second-order differential value ($D_{max}'$) and a minimum second-order differential value ($D_{min}'$) from the second-order differential values in a predetermined temperature range including a Tm value of the objective nucleic acid among the second-order differential values calculated in the above step and obtaining the maximum difference (B) based on the following formula $$B=(D_{max}')-(D_{min}');$$

calculating the following formula using the maximum value (A) and the maximum difference (B), $$X=(B)/(A); \text{ and}$$

determining that the objective nucleic acid has been amplified normally when X satisfies a condition [X>predetermined threshold value] and the objective nucleic acid has been amplified poorly when X satisfies a condition [X≦predetermined threshold value].

According to the present invention, whether or not an objective nucleic acid has been amplified can be determined easily by utilizing calculation such as the second-order differentiation and the like described above. Therefore, it becomes possible to avoid the conventional problems that criteria of determination vary between individuals who conduct determinations and specialized knowledge is required. Further, since whether or not an objective nucleic acid has been amplified can be easily determined, it is possible to cancel a melting curve analysis to be conducted thereafter with respect to a sample exhibiting poor amplification that leads to incorrect determination of genotype. Thus, ultimately, the melting curve analysis can be conducted more easily and with high reliability. Especially, by incorporating the system of the present invention in a conventional gene analysis device or the like, not only checking the presence or absence of amplification, but also conducting an operation from amplification of a nucleic acid to determination of a genotype in a fully automated manner becomes possible, for example. Therefore, for example, the present invention is expanded also to the field of general analysis and diagnosis, and allows the analysis with respect to a large number of specimens to be conducted easily. Thus, it can be said that the present invention is very useful technology especially in the field of gene analysis.

BEST MODE FOR CARRYING OUT THE INVENTION

Figure 1:
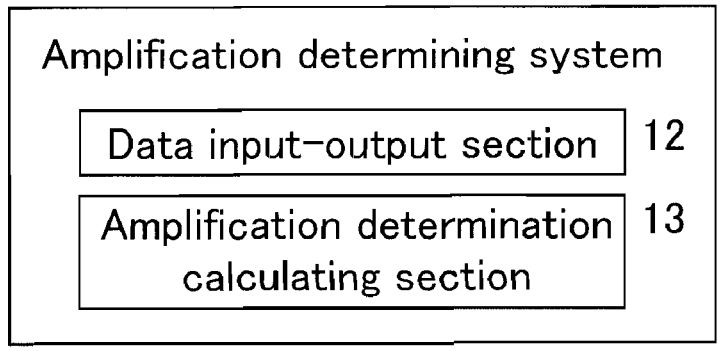
FIG. 1 shows an overall configuration of one example of a stand-alone type device using a system of the present invention.

In the present invention, signals showing the molten states of a sample may be generated by unmelting of the sample and the generation of the signals may be suppressed by melting of the sample, or on the other hand, the generation of the signals may be suppressed by unmelting of the sample and the signals may be generated by melting of the sample, for example. In the present invention, the signal differential value may be represented by, for example, "dF/dT" or "−dF/dT". The dF shows the amount of change in signal value, and the dT shows the amount of change in temperature. When the generation of the signals is suppressed by melting of the sample, a valley-shaped peak is shown in the melting curve representing the signal differential values by "dF/dT", and a mountain-shaped peak is shown in the melting curve representing the signal differential values by "−dF/dT". On the other hand, when the signals are generated by melting of the sample, a mountain-shaped peak is shown in the melting curve representing the signal differential values by "dF/dT", and a valley-shaped peak is shown in the melting curve representing the signal differential values by "−dF/dT" Regardless of whether signals are generated by either melting or unmelting of a sample, and whether signal differential values are represented by either of the formulae, the magnitude of the peak can be evaluated by the magnitude of the absolute value of the signal differential value.

In the present invention, the type of the signal value is not particularly limited, and examples thereof include an absorbance (an absorption intensity), a fluorescent intensity, and the like. Specific examples of the signal include the absorbance at 260 nm, which is increased by melting of a double strand, as described above, for example. When a fluorescent substance is used, the signal values may be intensities of fluorescence that is emitted by irradiation of excitation light depending on the fluorescent substance. The fluorescent substance may generate fluorescence by formation of a double strand (unmelting) or melting of the double strand. Specific examples of the fluorescent substance include intercalaters such as ethidium bromide and SYBR (registered trademark) Green. These fluorescent substances generally generate fluorescence by formation of a double strand (unmelting) and the generation of fluorescence is suppressed by melting of the double strand. In addition, the fluorescent substance may bind to at least one of single-stranded nucleic acids composing a double-stranded nucleic acid. The single-stranded nucleic acid with the fluorescent substance binding thereto can be, for example, a so-called fluorescence quenching probe such as Qprobe (registered trademark) known as a guanine quenching probe. In the fluorescence quenching probe, generally, quenching of fluorescence occurs by formation of a double strand and the fluorescence is generated by melting of the double strand. It is to be noted that the present invention is characterized by the processing of signal values, and the type of the signals and the like are not limited at all.

<Amplification Determining Method>

The amplification determining method of the present invention will be explained with reference to one example where an objective nucleic acid to be amplified (hereinafter referred to as "target nucleic acid") is a nucleic acid having a polymorphism in a target site and a Tm value of the objective nucleic acid is a Tm value of a double-stranded nucleic acid composed of the nucleic acid having a polymorphism in a target site and a nucleic acid that can hybridize to the target site (hereinafter referred to as "detection nucleic acid"). It is to be noted that the present invention is not limited to this example.

Step of Providing Signal Values

First, signal values showing molten states of the treated sample at respective temperatures are provided.

The temperature intervals of the signal values are not particularly limited, and are, for example, from 0.1° C. to 5° C., preferably from 0.2° C. to 3° C., and more preferably from 0.8° C. to 1.2° C. The temperature intervals may be different from each other. However, the temperature intervals preferably are equal to each other.

Signal values preferably are provided in the temperature range including a Tm value. When the target site has a polymorphism, a $Tm_H$ value that is relatively high and a $Tm_L$ value that is relatively low are presumed as Tm values of a double-stranded nucleic acid composed of the target nucleic acid and the detection nucleic acid as will be described later. Therefore, signal values preferably are provided, for example, in a wide temperature range including the $Tm_H$ value and the $Tm_L$ value. The temperature range is such that, for example, the lower limit thereof is preferably from 1° C. to 20° C. lower than the $Tm_L$ value, more preferably from 1° C. to 10° C. lower than the same, and the upper limit thereof is preferably from 1° C. to 20° C. higher than the $Tm_H$ value, more preferably from 1° C. to 10° C. higher than the same. As a specific example, the temperature range is preferably from [$Tm_L$ value −5]° C. to [$Tm_H$ value +5]° C.

When the target site has a polymorphism, as the target nucleic acid, a target nucleic acid with the wild-type target site (hereinafter referred to as "wild-type target nucleic acid") and a target nucleic acid with the mutant-type target site (hereinafter referred to as "mutant-type target nucleic acid") are presumed. Since the difference between the wild-type target nucleic acid and the mutant-type target nucleic acid is generally only a single base in the target site, a $Tm_H$ value of a double strand in which the target nucleic acid is a 100% match to the detection nucleic acid and a $Tm_L$ value of a double strand in which the target nucleic acid has a single-base mismatch to the detection nucleic acid are presumable as Tm values of the double-stranded nucleic acid, for example. Since the Tm value becomes higher as the homology of a double stranded becomes higher and becomes lower as the homology of a double stranded becomes lower, the $Tm_H$ value is higher than the $Tm_L$ value. As a specific example, in the case where, for example, a detection nucleic acid that can hybridize to a mutant-type target site (hereinafter referred to as "mutant-type detection nucleic acid") is used, a Tm value of a double-stranded nucleic acid composed of a mutant-type target nucleic acid and the mutant-type detection nucleic acid and a Tm value of a double-stranded nucleic acid composed of a wild-type target nucleic acid and the mutant-type detection nucleic acid are presumed as Tm values of the double-stranded nucleic acid. In this case, the former Tm value is a $Tm_H$ value, and the latter Tm value is a $Tm_L$ value. On the other hand, in the case where a detection nucleic acid that can hybridize a wild-type target site (hereinafter referred to as "wild-type detection nucleic acid") is used, a Tm value of a double-stranded nucleic acid composed of a wild-type target nucleic acid and the wild-type detection nucleic acid and a Tm value of a double-stranded nucleic acid composed of a mutant-type target nucleic acid and the wild-type detection nucleic acid are presumed as Tm values of the double-stranded nucleic acid. In this case, the former Tm value is a $Tm_H$ value, and the latter Tm value is a $Tm_L$ value. The above-described Tm values can be determined as appropriate depending on the sequence of the target nucleic acid, the sequence of the detection nucleic acid, and the like, and specifically, they can be calculated by the conventionally known MELTCALC software (meltcalc.com/) or the like, or can be determined by Nearest Neighbor Method (hereinafter the same). In the present embodiment, signal values showing molten states of a treated sample can be referred to as, for example, signal values showing molten states of a double-stranded nucleic acid composed of an amplification product of the target nucleic acid in the treated sample and a detection nucleic acid that can hybridize to the target nucleic acid.

Step of Searching for the Maximum Value (A)

Next, the maximum value (A) is searched for in the signal values at respective temperatures. At this time, if the maximum value (A) cannot be found, it can be determined that the amplification has been conducted poorly.

Step of Calculating Differential Values

Next, differential values of the signal values at the respective temperatures are calculated by differentiation of successive signal values. The differentiation is not particularly limited, and is, for example, preferably the differentiation of the signal values at two to ten successive points, more preferably two to five successive points, and particularly preferably two successive points. For example, in the case where the differentiation of signal values at two points is performed, a differential value ($D_p$) at an arbitrary point (p) may be a differential value calculated by the differentiation of a signal value ($S_p$) at the arbitrary point (p) and a signal value ($S_{p+1}$) at a point (p+1) adjacent to the point (p) or by the differentiation of the signal value ($S_p$) at the arbitrary point (p) and a signal value ($S_{p-1}$) at a point (p−1) adjacent to the point (p). However, it is preferable that differential values at respective points are calculated in the same manner. In the former case, p is a positive integer, and in the latter case, p is a positive integer of two or more.

Step of Calculating Second-Order Differential Values

Further, with respect to the differential values calculated in the above step, differentiation of the differential values at multiple successive points is performed, thereby obtaining second-order differential values. The differentiation of the differential values can be, for example, preferably the differentiation of the differential values at two to ten successive points, more preferably three to seven successive points, still more preferably three to five successive points, and particularly preferably four successive points. As a specific example, in the case where differentiation of the differential values at four points is performed, a second-order differential value ($D_p'$) at an arbitrary point (p) may be a second-order differential value in any of the following examples 1, 2, and 3, and it is preferable that second-order differential values at respective points are calculated in the same manner. A second-order differential value ($D_p'$) at an arbitrary point (p) may be calculated by, for example, the differentiation of the differential values at a total of four points, namely, points (p), (p+1), (p+2) and (p+3), as an example 1: the differentiation of the differential values at a total of four points, namely, points (p−1), (p), (p+1), and (p+2), as an example 2: and the differentiation of the differential values of at a total of four points, namely points (p−2), (p−1), p, and (p+1), as an example 3. The point (p) is a positive integer in the example 1, a positive integer of two or more in the example 2, and a positive integer of three or more in the example 3.

Step of Calculating the Maximum Difference (B)

Among the second differential values calculated in the above step, from those in a predetermined temperature range including a Tm value of the objective nucleic acid, the maximum second differential value ($D_{max}'$) and the minimum second differential value ($D_{min}'$) are selected. Then, the maximum difference (B) is calculated based on the following formula:

$$(B) = (D_{max}') - (D_{min}').$$

The predetermined temperature range is not limited as long as it includes a Tm value of the objective nucleic acid, and in the present embodiment, as described above, the temperature range includes both the $Tm_H$ value and the $Tm_L$ value, for example. As a specific example, the lower limit of the temperature range is preferably from 1° C. to 20° C. lower than a $Tm_L$ value, more preferably from 1° C. to 10° C. lower than the same, and still more preferably [$Tm_L$ value −5]° C. The upper limit of the temperature range is preferably from 1° C. to 20° C. higher than a $Tm_H$ value, more preferably from 1° C. to 10° C. higher than the same, and still more preferably [$Tm_H$ value +5]° C. In the present step, the maximum second-order differential value and the minimum second-order differential value may be selected from the second-order differential values in the predetermined temperature range. Therefore, for example, in the above-described step of calculating second-order differential values, calculating only second-order differential values in the predetermined temperature range is sufficient. Further, also in the above-described step of calculating differential values, calculating only differential values in a range in which second-order differential values in the predetermined temperature range can be calculated is sufficient.

Step of Calculating X

The calculation of the following formula is performed using the maximum value (A) and the maximum difference (B):

$$X = (B)/(A).$$

Step of Determination

It is determined that the objective nucleic acid has been amplified normally (normal amplification) when X satisfies a condition [X>predetermined threshold value] and the objective nucleic acid has been amplified poorly (poor amplification) when X satisfies a condition [X≦predetermined threshold value]. It is to be noted that, in the present invention, normal amplification means the state where a target nucleic acid has been amplified and it is considered that a reliable gene analysis can be conducted, and poor amplification means the state where a target nucleic acid has not been amplified or has not been amplified substantially, a different nucleic acid has been amplified, or the like, and it is considered that a reliable gene analysis cannot be conducted, or there is a risk of it.

The threshold value can be set as appropriate depending on a type of the signal, the detection wavelength of the signal, the type of a fluorescent substance that generates signals (fluorescence), the type of a nucleic acid to be amplified or a polymorphism in a target site thereof, the sequence of a detection nucleic acid, the composition of a reaction solution at the time when a double-stranded nucleic acid is formed, and the like. The present invention is not characterized by a specific threshold value or a method for setting the specific threshold value and is not limited thereby. One example of the method for setting the threshold value will be described later.

The amplification determining method of the present invention preferably further includes a step of outputting information of the obtained determination result, for example. The determination result can be an item as to whether normal amplification or not, for example. At the time of output, only the determination result may be outputted, or the value of X, a graph of a melting curve plotting temperatures and differential values, a graph plotting temperatures and second-order differential values, and the like also may be outputted with the determination result.

As the signal values in the above-described step of providing signal values, the data previously obtained by detection may be used, for example, and they may be provided by detecting signal values prior to the steps of providing signal values, for example. Specifically, the amplification determining method further may include, prior to the step of providing signal values, the step of changing a temperature of the sample treated so as to amplify the nucleic acid (for example, a double-stranded nucleic acid); and detecting continuously or intermittently signal values showing molten states of the sample at the time of temperature change. The step of changing a temperature may be, for example, a step of heating the sample or a step of cooling the heated sample. However, the step of changing a temperature preferably is the step of heating the sample.

In addition, prior to the step of changing a temperature, the method may include a step of amplifying a nucleic acid in a sample. In this case, for example, the detection nucleic acid described above may be added to the sample treated so as to amplify a nucleic acid. However, the detection nucleic acid preferably is added to the sample prior to the treatment so as to amplify the nucleic acid because this allows a continuous operation.

Figure 6:
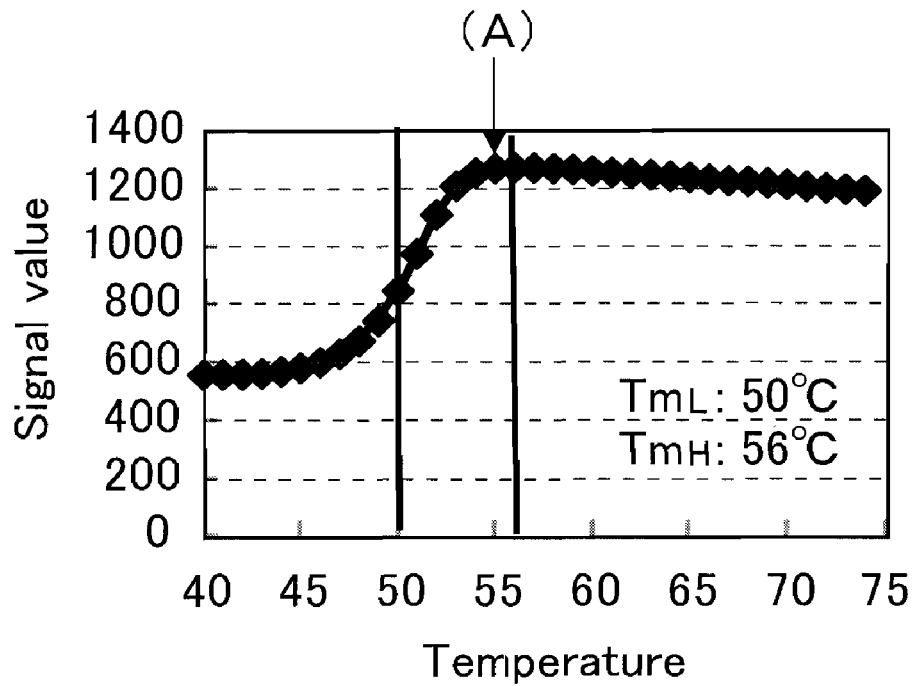
FIG. 6 is a graph showing a melting curve in an embodiment of the present invention.
Figure 7:
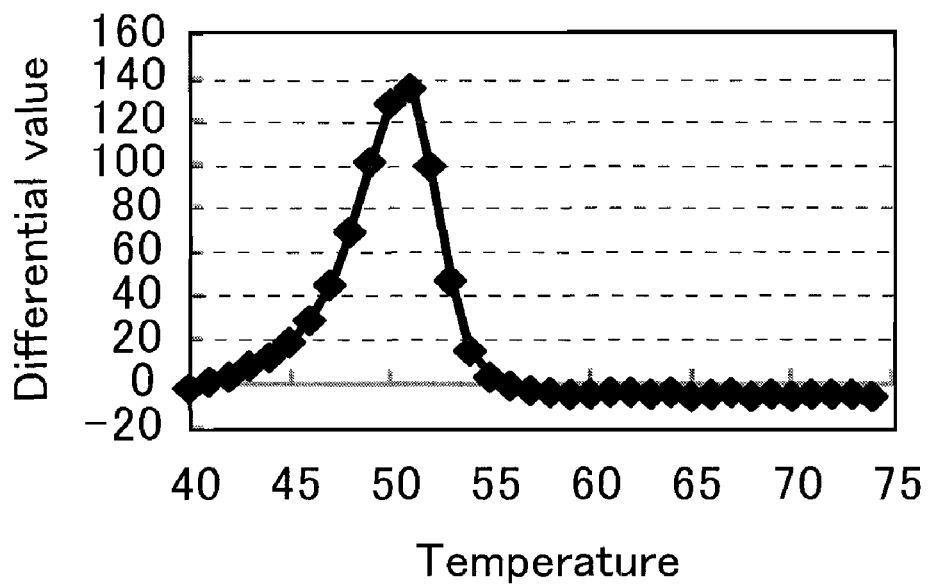
FIG. 7 is a graph showing a differential curve in an embodiment of the present invention.
Figure 8:
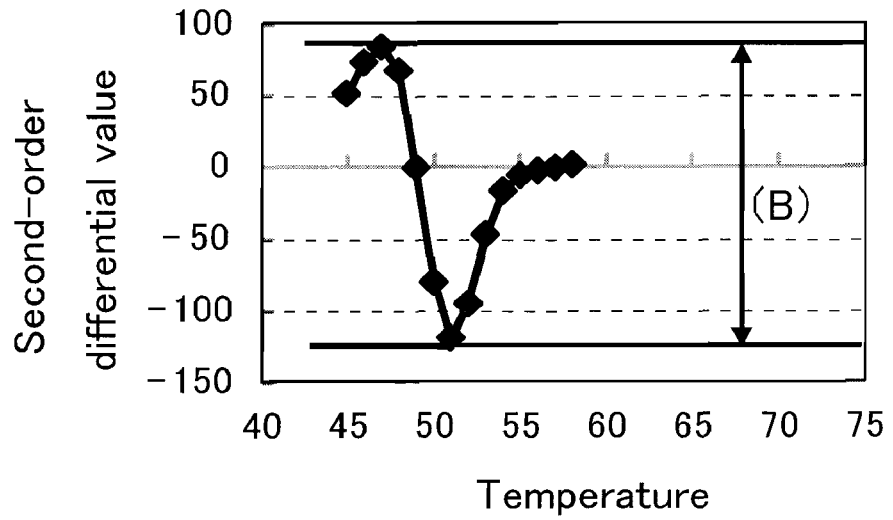
FIG. 8 is a graph showing a second-order differential curve in an embodiment of the present invention.

The amplification determining method of the present invention will be explained further specifically with reference to graphs shown in FIGS. 6, 7, and 8 as examples. FIG. 6 is a graph showing the relationship between temperatures and signal values (melting curve), FIG. 7 is a graph showing the relationship between temperatures and signal differential values (differential curve), and FIG. 8 is a graph showing the relationship between temperatures and second-order differential values (second-order differential curve). The signal value is assigned to the vertical axis in FIG. 6, the signal differential value is assigned to the vertical axis in FIG. 7, the second-order differential value is assigned to the vertical axis in FIG. 8, and the temperature is assigned to the horizontal axis in each figure. Further, the relatively low $Tm_L$ value was set to 50° C., the relatively high $Tm_H$ value was set to 56° C., and the temperature range in the step of calculating the maximum difference (B) was set to 45° C. ($Tm_L$ value −5° C.) to 61° C. (Tm$_H$ value +5° C.). It is to be noted that these are merely illustrative and do not limit the present invention.

A graph showing the relationship between temperatures and signal values at the respective temperatures is provided as shown in FIG. 6, and the maximum value (A) is searched for. On the other hand, the signal values are differentiated, and a graph showing the relationship between temperatures and the differential values at the respective temperatures is provided as shown in FIG. 7. Next, the differential values are differentiated, and a graph showing the relationship between the temperatures in the temperature range from 45° C. to 61° C. and the second-order differential values at the respective temperature is provided as shown in FIG. 8. Subsequently, the maximum second-order differential value ($D_{max}'$) and the minimum second-order differential value ($D_{min}'$) are selected in the graph of FIG. 8, and the maximum difference (B) among the second-order differential values is calculated based on the formula (B)=($D_{max}'$)−($D_{min}'$). Further, the calculation of the formula "X=(B)/(A)" is performed using the maximum value (A) and the maximum difference (B). The amplification is determined as normal amplification when the calculated X satisfies the condition [X>predetermined threshold value], and the amplification is determined as poor amplification when the calculated X satisfies the condition [X≦predetermined threshold value]. With respect to only the sample treated so as to amplify the nucleic acid and determined as a sample with normal amplification, a melting curve analysis to be described later may be performed to determine the polymorphism, for example.

FIGS. 6, 7, and 8 are directed to an example where signal values increase with dissociation of a double-stranded nucleic acid caused by temperature increase. However, also in the case where signal values decreases with dissociation of a double-stranded nucleic acid caused by temperature increase, it is possible to determine whether the amplification is normal or poor by determining the maximum value (A) among the signal values and the maximum difference (B) among the second-order differential values and calculating X in the same manner. It is to be noted that, although three types of graphs are exemplified in this example, it is not essential to prepare the various graphs in the present invention.

In the present invention, the threshold value of X is not limited at all as described above and can be determined as appropriate depending on the type of a target nucleic acid (gene), the type of a polymorphism, and the like. Hereinafter, a method for setting the threshold value will be described by way of example. However, the present invention is not limited thereto.

Figure 9:
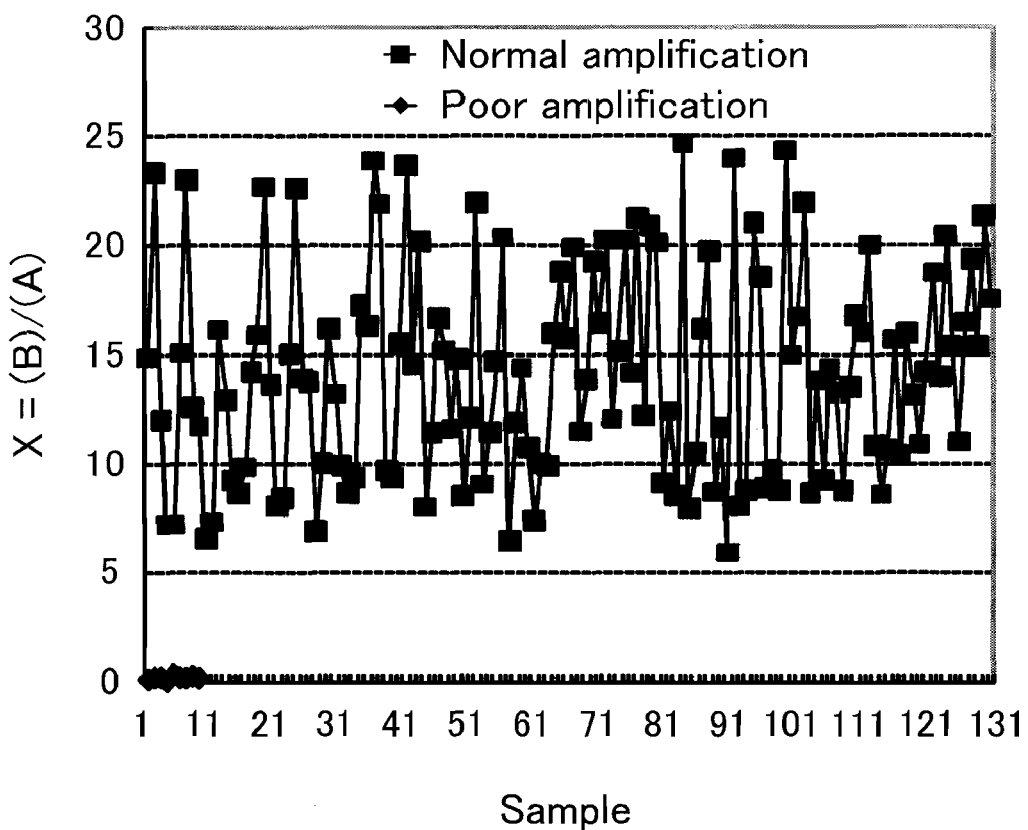
FIG. 9 is a graph showing a formula X=(B)/(A) in an embodiment of the present invention.

The threshold value of X can be determined as below, for example. First, multiple nucleic acid specimens are subjected to a nucleic acid amplification treatment, and whether the amplification of the target nucleic acids is normal or poor is checked. Further, with respect to a double strand composed of an amplification product obtained from each of the nucleic acid specimens and a detection nucleic acid, signal values at respective temperatures are detected, and the determination of the maximum value (A) and the maximum difference (B) and the calculation of X=(B)/(A) are performed in the same manner as described above. Then, a graph plotting Xs of each nucleic acid specimen is prepared. One example of this graph is shown in FIG. 9. As shown in FIG. 9, Xs of the nucleic acid specimens with normal amplification (■) and Xs of the nucleic acid specimens with poor amplification (♦) are distinctly different. Thus, a critical value between Xs of normal amplification and Xs of poor amplification may be determined from this graph and set to a threshold value.

In the amplification determining method of the present invention, the objective nucleic acid is not limited to a target nucleic acid that has a polymorphism in the target site and is presumed to have two Tm values. When one Tm value is presumed, the temperature range including the Tm value in the step of calculating the maximum difference (B) is such that, for example, the lower limit thereof is preferably from 1° C. to 20° C. lower than the Tm value, more preferably from 1° C. to 10° C. lower than the same, and still more preferably [Tm value −5]° C. The upper limit of the temperature range is preferably from 1° C. to 20° C. higher than the Tm value, more preferably from 1 to 10° C. higher than the same, and still more preferably [Tm value +5]° C.

The amplification determining method of the present invention further may include the step of analyzing a melting curve of the sample treated so as to amplify a nucleic acid, thereby determining whether or not a peak is present in the predetermined temperature range. Thus, with respect to only the sample determined as the sample being amplified normally, a melting curve analysis can be conducted to carry out a polymorphism analysis (genotype analysis), for example. As described above, according to the method of the present invention, since the necessity of conducting a melting curve analysis with respect to the sample with poor amplification can be eliminated, the melting curve analysis can be conducted more rapidly and more efficiently than ever before. Furthermore, when the present invention includes the step of analyzing a melting curve, an operation from the determination of nucleic acid amplification to the melting curve analysis and the determination of a polymorphism (genotype) with respect to a sample determined as a sample with normal amplification, for example, can be conducted continuously. Therefore, the amplification determining method of the present invention also can be referred to as a melting curve analysis method or a polymorphism analysis method (or a genotype analysis method).

For example, the amplification determining method of the present invention can be achieved by, for example, an amplification determining system of the present invention, an amplification determining device of the present invention, and running a computer program of the present invention.

<Amplification Determining System>

An amplification determining system of the present invention is an amplification determining system for determining whether or not an objective nucleic acid has been amplified with respect to a sample treated so as to amplify the nucleic acid, including:

a signal value input section for inputting signal values showing molten states of the treated sample at respective temperatures;

a maximum value (A) searching section for searching for a maximum value (A) in the signal values at the respective temperatures inputted by the signal value input section;

a differential value calculating section for calculating differential values of the signal values at the respective temperatures by differentiation of successive signal values;

a second-order differential value calculating section for calculating second-order differential values of the differential values calculated in the differential value calculating section by differentiation of successive differential values;

a maximum difference (B) calculating section for calculating a maximum difference (B) among the second-order differential values by selecting a maximum second-order differential value ($D_{max}'$) and a minimum second-order differential value ($D_{min}'$) from the second-order differential values in a predetermined temperature range including a Tm value of the objective nucleic acid among the second-order differential values calculated in the second-order differential value calculating section and obtaining the maximum difference (B) based on the following formula $$B=(D_{max}')-(D_{min}');$$

a calculation section for calculating the following formula using the maximum value (A) and the maximum difference (B):

$$X=(B)/(A); \text{ and}$$

a determination section for determining that the objective nucleic acid has been amplified normally when X satisfies a condition [X>predetermined threshold value] and the objective nucleic acid has been amplified poorly when X satisfies a condition [X≦predetermined threshold value]. It is to be noted that the amplification determining system of the present invention is the same as the amplification determining method unless otherwise stated.

In the amplification determining system of the present invention, the differential values preferably are calculated by, for example, differentiation of the signal values of successive two points in the differential value calculating section, and the seconds differential values preferably are calculated by, for example, differentiation at successive four points in the differential value calculating section.

In the amplification determining system of the present invention, the objective nucleic acid preferably is a nucleic acid having a polymorphism in a target site. Further, a Tm value of the objective nucleic acid preferably is a Tm value of a double-stranded nucleic acid composed of the nucleic acid having a polymorphism in the target site (target nucleic acid) and the detection nucleic acid. When the detection nucleic acid is a wild-type detection nucleic acid, Tm values of the objective nucleic acid are, for example, a $Tm_H$ value of a double-stranded nucleic acid composed of the wild-type target nucleic acid and the wild-type detection nucleic acid and a $Tm_L$ value of a double-stranded nucleic acid composed of the mutant-type target nucleic acid and the wild-type detection nucleic acid. On the other hand, when the detection nucleic acid is a mutant-type detection nucleic acid, Tm values of the objective nucleic acid is, for example, a $Tm_H$ value of a double-stranded nucleic acid composed of the mutant-type target nucleic acid and the mutant-type detection nucleic acid and a $Tm_L$ value of a double-stranded nucleic acid composed of the wild-type target nucleic acid and the mutant-type detection nucleic acid.

In the maximum difference (B) calculation section, the predetermined temperature range including a Tm value of the objective nucleic acid is such that, for example, the lower limit thereof is from 1° C. to 20° C. lower than a $Tm_L$ value, and the upper limit is from 1° C. to 20° C. higher than a $Tm_H$ value. The temperature range preferably is from [$Tm_L$ value −5]° C. to [$Tm_H$ value +5]° C.

The amplification determining system of the present invention further may include a temperature changing section for changing a temperature of the sample treated so as to amplify the nucleic acid, and a detection section for detecting continuously or intermittently signal values showing molten states of the treated sample at the time of temperature change. The temperature changing section may be, for example, a heating section for heating the sample or a cooling section for cooling the heated sample. Examples of the temperature changing section include a temperature controller, a heater, a thermal cycler, and the like that can adjust a temperature, and examples of the detection section include a spectrophotometer, a fluorometer, and the like. Further, examples of a section including both of the sections include measuring instruments used for a real-time PCR, and the like. Preferably, the signals are fluorescence, and the detection section detects the fluorescence, for example.

The amplification determining system of the present invention further may include: a nucleic acid amplification section for treating a sample so as to amplify the nucleic acid.

The amplification determining system of the present invention may include: an addition section for, when the objective nucleic acid is a nucleic acid having a polymorphism in a target site, adding a nucleic acid that can hybridize to the target site to the sample.

The amplification determining system of the present invention further may include a melting curve analysis section for analyzing a melting curve of the sample treated so as to amplify the nucleic acid to analyze whether or not a peak is present in the predetermined temperature range.

The amplification determining system of the present invention preferably further includes an output section for outputting information of the obtained determination result, for example. The determination result includes an item as to whether normal amplification or not, for example. At the time of output, only the determination result may be outputted, or the value of X, a graph of a melting curve plotting temperatures and differential values, a graph plotting temperatures and second-order differential values, and the like also may be outputted with the determination result.

<Amplification Determining Network System and Terminal Used Therefor>

The amplification determining system of the present invention may be a network system including a terminal and a server that are described below. It is to be noted that the system is the same as in the above-described amplification determining system unless otherwise stated. That is, the amplification determining system of the present invention is an amplification determining network system for analyzing whether or not an objective nucleic acid has been amplified with respect to a sample treated so as to amplify the nucleic acid, including;

a terminal; and a server, wherein the terminal and the server are connectable through a communication network that is outside of the system, the terminal includes;

a signal value input section for inputting signal values showing molten states of the treated sample at respective temperatures;

a terminal-side transmitting section for transmitting information in the terminal to the server through the communication network; and a terminal-side receiving section for receiving the information transmitted from the server through the communication network, the server includes:

a server-side transmitting section for transmitting information in the server to the terminal through the communication network;

a server-side receiving section for receiving the information transmitted from the terminal through the communication network;

a maximum value (A) searching section for searching for a maximum value (A) in the signal values at respective temperatures received by the server-side receiving section;

a differential value calculating section for calculating differential values of the signal values at the respective temperatures by differentiation of successive signal values;

a second-order differential value calculating section for calculating second-order differential values of the differential values calculated in the differential value calculating section by differentiation of successive differential values;

a maximum difference (B) calculating section for calculating a maximum difference (B) among the second-order differential values by selecting a maximum second-order differential value ($D_{max}'$) and a minimum second-order differential value ($D_{min}'$) from the second-order differential values in a predetermined temperature range including a Tm value of the objective nucleic acid among the second-order differential values calculated in the second-order differential value calculating section and obtaining the maximum difference (B) based on the following formula $$B=(D_{max}')-(D_{min}');$$

a calculation section for calculating the following formula using the maximum value (A) and the maximum difference (B):

$$X=(B)/(A); \text{ and}$$

a determination section for determining that the objective nucleic acid has been amplified normally when X satisfies a condition [X>predetermined threshold value] and the objective nucleic acid has been amplified poorly when X satisfies a condition [X≦predetermined threshold value]. In the system, at least the signal values at the respective temperatures are transmitted from the terminal-side transmitting section to the server-side receiving section, and information of the determination result as to whether the amplification is normal or poor is transmitted from the server-side transmitting section to the terminal-side receiving section.

The terminal of the present invention is a terminal used for the amplification determining network system of the present invention. The terminal includes:

a differential value input section for inputting signal values showing molten states of the sample at respective temperatures;

a terminal-side transmitting section for transmitting information in the terminal to the server through the communication network; and a terminal-side receiving section for receiving the information transmitted from the server through the communication network. In the system, at least the signal values at the respective temperatures are transmitted from the terminal-side transmitting section to the server-side receiving section, and information of the determination result as to whether the amplification is normal or poor is transmitted from the server-side transmitting section to the terminal-side receiving section.

<Amplification Determining Device>

An amplification determining device of the present invention is an amplification determining device for determining whether or not an objective nucleic acid has been amplified with respect to a sample treated so as to amplify the nucleic acid, including the amplification determining system of the present invention.

<Program>

A program of the present invention is a computer program that can execute the amplification determining method of the present invention on a computer.

<Electronic Medium>

An electronic medium of the present invention is an electronic medium storing the computer program of the present invention.

Next, examples of the present invention will be explained.

First Example of System Configuration

Figure 3:
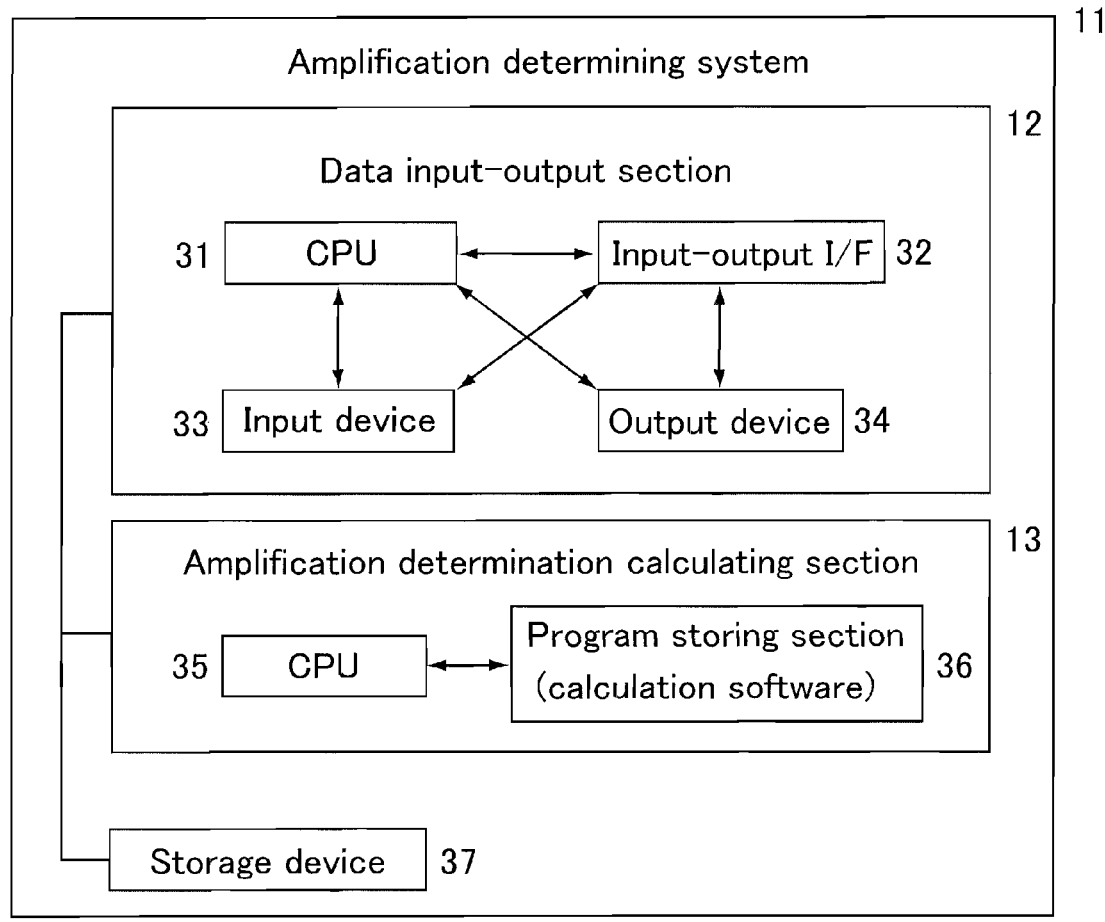
FIG. 3 is a block diagram showing one example of a configuration of the stand-alone type device.

FIG. 1 shows an overall configuration of a stand-alone type system as one example of a configuration of a system of the present invention. The system shown in FIG. 1 includes an amplification determining system 11 of the present invention, and the amplification determining system 11 includes a data input-output section 12 and an amplification determination calculating section 13. FIG. 3 shows one example of a hardware configuration of a stand-alone type amplification determining device. As shown in FIG. 3, the amplification determining system 11 includes a data input-output section 12, an amplification determination calculating section 13, and a storage device 37. The data input-output section 12 includes computer equipment including a CPU 31 for running a program, an input-output I/F (interface) 32, an input device 33 for inputting data, and an output device 34 for outputting data. Examples of the input device 33 include a keyboard, a mouse, and the like, and examples of the output device 34 include a printer, a LED display or a liquid crystal display, and the like. The amplification determination calculating section includes computer equipment including a program storing section 36 in which a program is stored and a CPU 35 for running the program. In the storage device 37, for example, the data such as signal values at respective temperatures, signal differential values, second-order differential values, Tm values ($Tm_H$ value, $Tm_L$ value), predetermined temperature ranges including the Tm values, the sequence of a detection probe and the type thereof (a wild-type detection probe or a mutant-type detection probe), and the like are stored in the call ready state. Examples of the storage device 37 include a ROM, a HDD, a HD, and the like, and the storage device 37 stores data while controlling reading/writing under the control of the CPU. It is to be noted that the data input-output section 12, the amplification determination calculating section 13, and the storage device 37 are merely functional, and for example, they may be configured integrally in one set of computer equipment or configured individually in multiple sets of computer equipment.

Further, the system of the present invention further may include a temperature changing section for changing a temperature of the sample (for example, a heat treatment section for conducting a heat treatment), and a detection section for detecting continuously and intermittently signal values showing molten states of the sample at the time of temperature change. Furthermore, the signal values detected in the detection section may be inputted by the data input-output section. Examples of the temperature changing section include a heating device and the like. Examples of the detection section include an optical photometer and a fluorometer. The heat treatment section and the detection section may be configured integrally in one set of computer equipment or configured individually in multiple sets of computer equipment.

The system of the present invention further may include a melting curve analyzing section for analyzing a melting curve of a sample treated so as to amplify the nucleic acid to analyze whether or not a peak is present in the predetermined temperature range. According to the system of the present invention including the melting curve analysis section, it is possible not only to determine whether the amplification is normal or poor but also to conduct a melting curve analysis with respect to the sample determined as the sample with normal amplification so as to determine a polymorphism (a genotype) of a target nucleic acid based on the presence or absence of a peak, for example. In addition, the system may include a nucleic acid extracting section for extracting a nucleic acid from a biological sample, an amplification treatment section for conducting a nucleic acid amplification reaction, and the like. With the foregoing configuration, it is possible to provide a nucleic acid amplification system that automatically can conduct an operation within the single system, for example, from amplification of a nucleic acid to determination of the amplification or from amplification of a nucleic acid to determination of a polymorphism (a genotype).

Second Example of System Configuration

Figure 2:
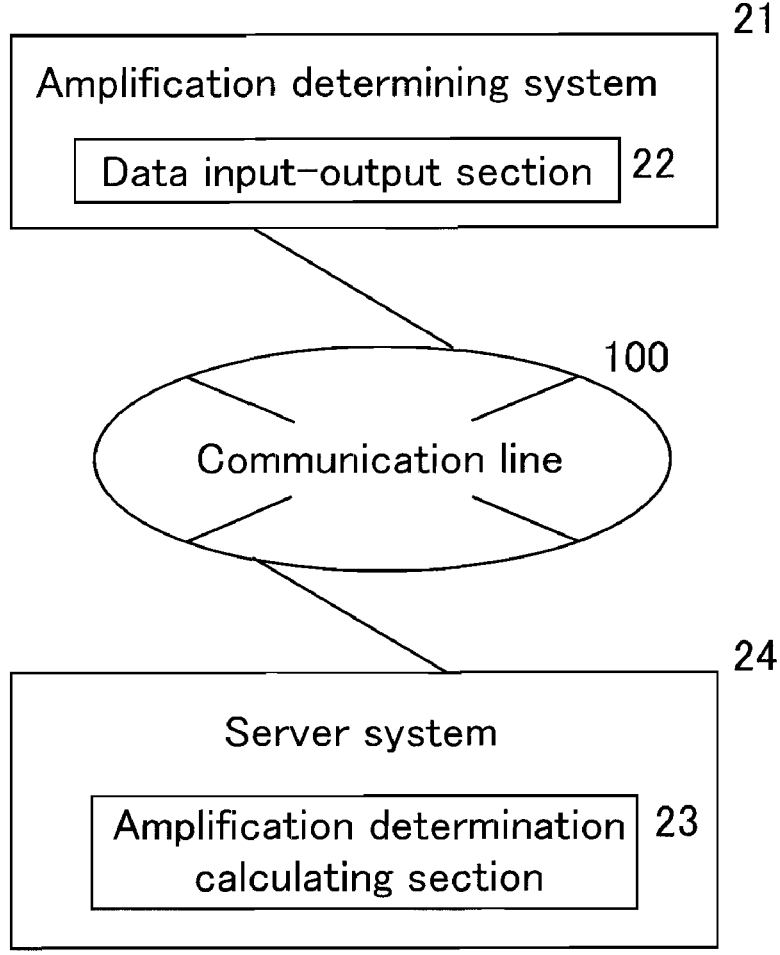
FIG. 2 shows an overall configuration of one example of a network-utilizing type device using the system of the present invention.
Figure 4:
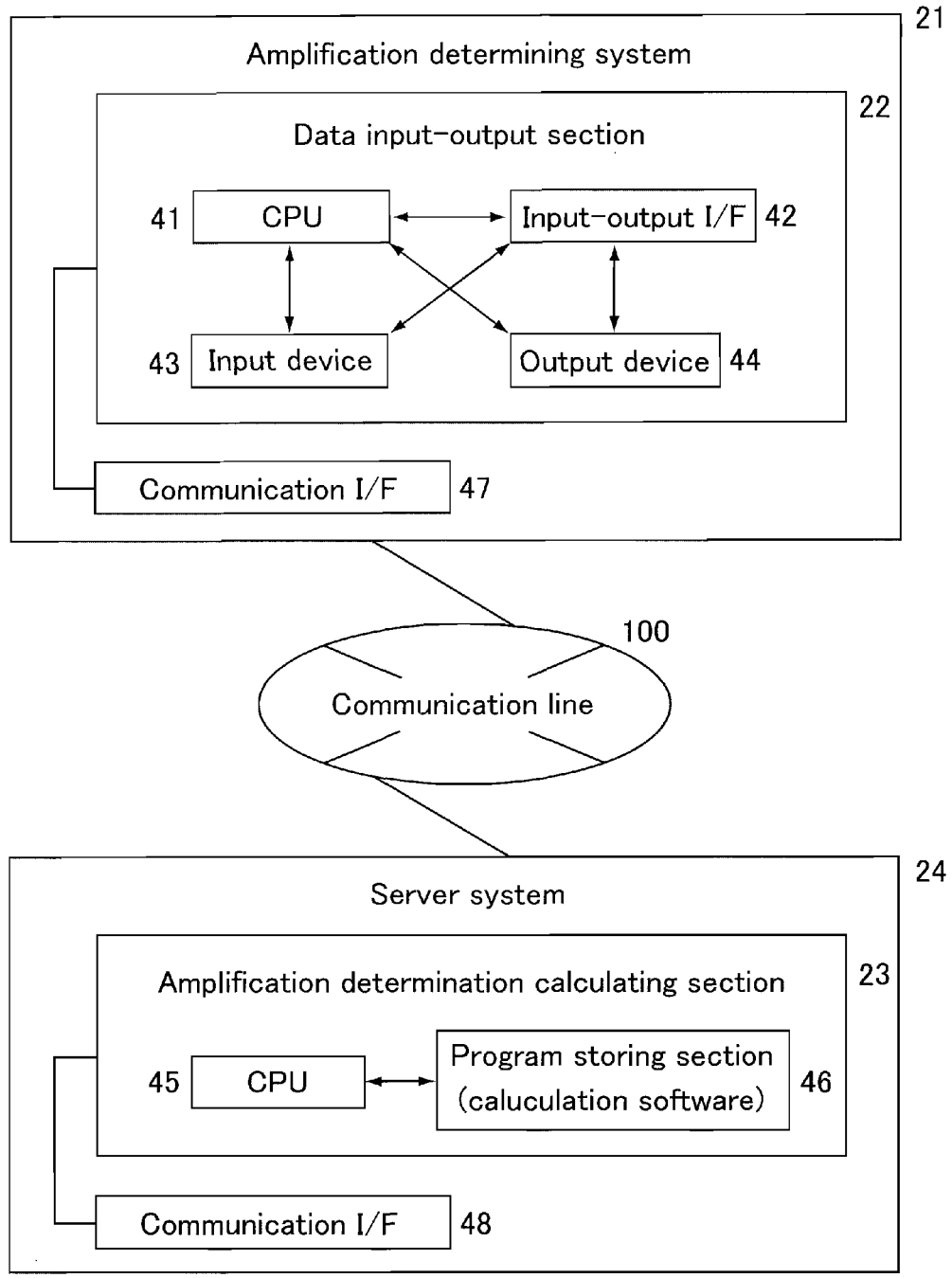
FIG. 4 is a block diagram showing one example of a configuration of the network-utilizing type device.

FIG. 2 shows an overall configuration of a network-type system that performs processing in a server. As shown in FIG. 2, the system of the present embodiment includes an amplification determining system 21 of the present invention and a server system 24 including an amplification determination calculating section 23. The amplification determining system 21 includes a data input-output section 22. The amplification determining system 21 and the server system 24 are connected through a communication line 100 such as a public network, a dedicated line, or the like that operates as the Internet based on TCP (Transmission Control Protocol)/IP (Internet Protocol). FIG. 4 shows one example of a device configuration of the network-utilizing type system. The amplification determining system 21 includes the data input-output section 22 and a communication I/F (interface) 47, and is connected to the communication line 100 through the communication I/F 47. The server system 24 includes the amplification determination calculating section 23 and a communication I/F 48, and is connected to the communication line 100 through the communication I/F 48. The data input-output section 22 includes a CPU 41 for running a program, an input-output I/F 42, an input device 43 for inputting data, and an output device 44 for outputting the data. The data input-output section 22 and the communication I/F 47 are illustrated in terms of function, and for example, they may be configured integrally in one set of computer equipment or configured individually in multiple sets of computer equipment. The amplification determination calculating section 23 includes a CPU 45 for running a program and a program storing section 46 in which the program is stored. The amplification determination calculating section 23 and the communication I/F 48 are illustrated in terms of function, and for example, they may be configured integrally in one set of computer equipment or configured individually in multiple sets of computer equipment.

Example of Basic Processing of System

Figure 5:
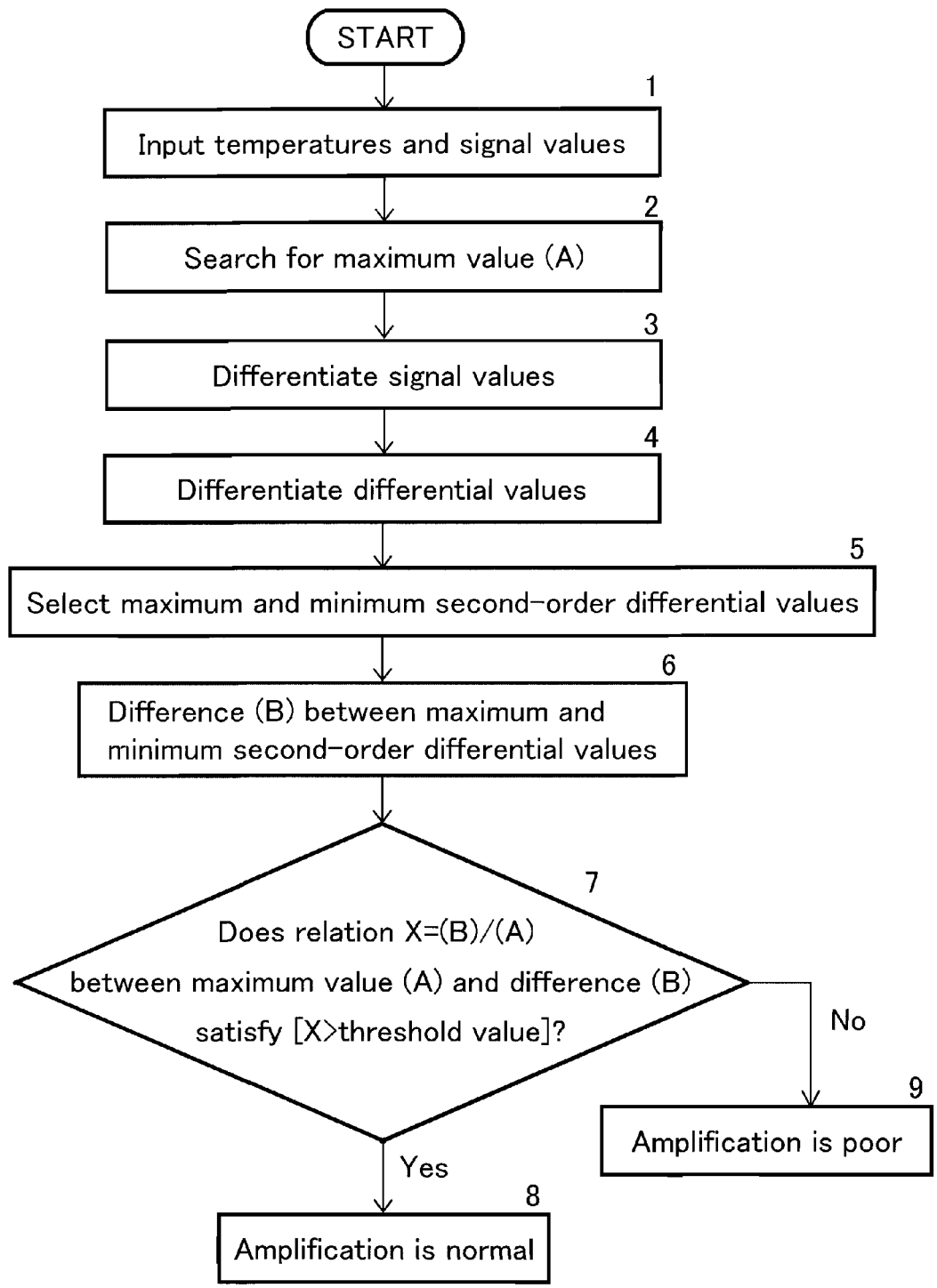
FIG. 5 shows one example of a flowchart for running the system of the present invention.

An example of basic processing of the amplification determining system of the present invention is shown in a flowchart of FIG. 5. Hereinafter, the flow of the processing will be explained following FIG. 5. It is to be noted that each processing step of the system of the present invention can be carried out by using: hardware components such as a CPU, a main memory, a bus or exterior peripheral devices like a secondary storage device, a printer, a display, and others; input-output (I/O) ports for the exterior peripheral devices; a driver program for controlling these hardware components and other application programs; and the like, as appropriate.

[1]
Signal values at respective temperatures are inputted.
[2]
The maximum signal value (A) is searched for.
[3]
The signal values at the respective temperatures are differentiated.
[4]
The signal differential values are differentiated further.
[5]
The maximum second-order differential value and the minimum second-order differential value are searched for in the second-order differential values.
[6]
The difference between the maximum second-order differential value and the minimum second-order differential value, i.e., the maximum difference (B) is obtained.
[7]
Whether or not X calculated using the maximum value (A) and the maximum difference (B) satisfies the condition [X>threshold value] is determined.
[8: Yes]
When [7] is Yes, it is determined that amplification is normal.
[9: No]
When [7] is No, it is determined that amplification is poor.

INDUSTRIAL APPLICABILITY

As above, according to the present invention, whether or not an objective nucleic has been amplified can be easily determined by utilizing calculation such as the second-order differentiation and the like described above. Therefore, it became possible to avoid the conventional problems that the criteria of determination vary between individuals who conduct determinations and specialized knowledge is required. Thus, since whether or not an objective nucleic acid has been amplified can be determined easily, it is possible to cancel a further melting curve analysis with respect to a sample exhibiting poor amplification that leads to incorrect determination. Thus, ultimately, the melting curve analysis can be conducted more easily and with high reliability. Especially, by incorporating the system of the present invention in a conventional gene analysis device or the like, not only checking the presence or absence of amplification, but also conducting an operation from amplification of a nucleic acid to determination of a genotype in a fully automated manner becomes possible, for example. Therefore, for example, the present invention also can be used in the field of general analysis and diagnosis, and the present invention allows the analysis with respect to a large number of specimens to be easily conducted. Thus, it can be said that the present invention is very useful technology especially in the field of gene analysis.

The invention claimed is:

1. An amplification determining method for determining whether or not an objective nucleic acid has been amplified with respect to a sample treated so as to amplify the nucleic acid, comprising the steps of:
provide signal values showing molten states of the treated sample at respective temperatures;
searching for a maximum value (A) in the signal values at the respective temperatures;
calculating using a computer differential values of the signal values at the respective temperatures by differentiation of successive signal values;

calculating second-order differential values of the differential values calculated in the above step by differentiation of successive differential values;

calculating a maximum difference (B) among the second-order differential values by selecting a maximum second-order differential value ($D_{max}'$) and a minimum second-order differential value ($D_{min}'$) from the second-order differential values in a predetermined temperature range including a Tm value of the objective nucleic acid among the second-order differential values calculated in the above step and obtaining the maximum difference (B) based on the following formula $$(B) = (D_{max}') - (D_{min}');$$

calculating the following formula using the maximum value (A) and the maximum difference (B);

$$X = (B)/(A); \text{ and}$$

determining that the objective nucleic acid has been amplified normally when X satisfies a condition [X>predetermined threshold value] and the objective nucleic acid has been amplified poorly when X satisfies a condition [X<predetermined threshold value].

2. The amplification determining method according to claim 1, wherein, in the step of calculating the differential values, the differential values are calculated by differentiation at two successive points.

3. The amplification determining method according to claim 1, wherein, in the step of calculating the second-order differential values, the second-order differential values are calculated by differentiation at four successive points.

4. The amplification determining method according to claim 1, wherein the objective nucleic acid is a nucleic acid having a polymorphism in a target site.

5. The amplification determining method according to claim 4, wherein the Tm value of the objective nucleic acid is a Tm value of a double-stranded nucleic acid composed of the nucleic acid having a polymorphism in a target site and a nucleic acid that can hybridize to the target site.

6. The amplification determining method according to claim 5, wherein, when the nucleic acid that can hybridize to the target site is a nucleic acid that can hybridize to the wild-type target site, the Tm values of the objective nucleic acid are a $Tm_H$ value of a double-stranded nucleic acid composed of a nucleic acid with the wild-type target site and the nucleic acid that can hybridize to the wild-type target site and a $Tm_L$ value of a double-stranded nucleic acid composed of a nucleic acid with the mutant-type target site and the nucleic acid that can hybridize to the wild-type target site, and when the nucleic acid that can hybridize to the target site is a nucleic acid that can hybridize to the mutant-type target site, the Tm values of the objective nucleic acid are a $Tm_H$ value of a double-stranded nucleic acid composed of a nucleic acid with the mutant-type target site and the nucleic acid that can hybridize to the mutant-type target site, and a $Tm_L$ value of a double-stranded nucleic acid composed of a nucleic acid with the wild-type target site and the nucleic acid that can hybridize to the mutant type target site.

7. The amplification determining method according to claim 6, wherein, in the step of calculating the maximum difference (B), a lower limit of the predetermined temperature range including the Tm value of the objective nucleic acid is from 1° C. to 20° C. lower than the $Tm_L$ value, and an upper limit of the same is from 1° C. to 20° C. higher than the $Tm_H$ value.

8. The amplification determining method according to claim 7, wherein the temperature range is from [$Tm_L$ value −5]° C. to [$Tm_H$ value +5]° C.

9. The amplification determining method according to claim 1, further comprising, prior to the step of providing signal values, the steps of;

changing a temperature of the sample treated so as to amplify the nucleic acid; and detecting continuously or intermittently signal values showing molten states of the treated sample at the time of temperature change.

10. The amplification determining method according to claim 9, wherein the objective nucleic acid is a nucleic acid having a polymorphism in a target site, and the method further comprises, prior to the step of changing the temperature, the step of: adding a nucleic acid that can hybridize to the target site to the sample.

11. An amplification determining system for determining whether or not an objective nucleic acid has been amplified with respect to a sample treated so as to amplify the nucleic acid, comprising:

a signal value input section for inputting signal values showing molten states of the treated sample at respective temperatures;

a maximum value (A) searching section for searching for a maximum value (A) in the signal values at the respective temperatures inputted by the signal value input section;

a differential value calculating section for calculating differential values of the signal values at the respective temperatures by differentiation of successive signal values;

a second-order differential value calculating section for calculating second-order differential values of the differential values calculated in the differential value calculating section by differentiation of successive differential values;

a maximum difference (B) calculating section for calculating a maximum difference (B) among the second-order differential values by selecting a maximum second-order differential value ($D_{max}'$) and a minimum second-order differential value ($D_{min}'$) from the second-order differential values in a predetermined temperature range including a Tm value of the objective nucleic acid among the second-order differential values calculated in the second-order differential value calculating section and obtaining the maximum difference (B) based on the following formula $$B = (D_{max}') - (D_{min}');$$

a calculation section for calculating the following formula using the maximum value (A) and the maximum difference (B):

$$X = (B)/(A); \text{ and}$$

a determination section for determining that the objective nucleic acid has been amplified normally when X satisfies a condition [X>predetermined threshold value] and the objective nucleic acid has been amplified poorly when X satisfies a condition [X≦predetermined threshold value].

12. The amplification determining system according to claim 11, wherein, in the differential value calculating section, the differential values are calculated by differentiation at two successive points.

13. The amplification determining system according to claim 11, wherein, in the second-order differential value calculating section, the second-order differential values are calculated by differentiation at four successive points.

14. The amplification determining system according to claim 11, wherein the objective nucleic acid is a nucleic acid having a polymorphism in a target site.

15. The amplification determining system according to claim 14, wherein the Tm value of the objective nucleic acid is a Tm value of a double-stranded nucleic acid composed of the nucleic acid having a polymorphism in a target site and a nucleic acid that can hybridize to the target site.

16. The amplification determining system according to claim 15, wherein, when the nucleic acid that can hybridize to the target site is a nucleic acid that can hybridize to the wild-type target site, the Tm values of the objective nucleic acid are a $Tm_H$ value of a double-stranded nucleic acid composed of a nucleic acid with the wild-type target site and the nucleic acid that can hybridize to the wild-type target site and a $Tm_L$ value of a double-stranded nucleic acid composed of a nucleic acid with the mutant-type target site and the nucleic acid that can hybridize to the wild-type target site, and when the nucleic acid that can hybridize to the target site is a nucleic acid that can hybridize to the mutant-type target site, the Tm values of the objective nucleic acid are a $Tm_H$ value of a double-stranded nucleic acid composed of a nucleic acid with the mutant-type target site and the nucleic acid that can hybridize to the mutant-type target site, and a $Tm_L$ value of a double-stranded nucleic acid composed of a nucleic acid with the wild-type target site and the nucleic acid that can hybridize to the mutant-type target site.

17. The amplification determining system according to claim 16, wherein, in the maximum difference (B) calculating section, a lower limit of the predetermined temperature range including the Tm value of the objective nucleic acid is from 1° C. to 20° C. lower than the $Tm_L$ value, and an upper limit of the same is from 1° C. to 20° C. higher than the $Tm_H$ value.

18. The amplification determining system according to claim 17, wherein the temperature range is from [$Tm_L$ value −5]° C. to [$Tm_H$ value +5]° C.

* * * * *